United States Patent
Unarce, Jr.

(10) Patent No.: US 9,002,479 B1
(45) Date of Patent: Apr. 7, 2015

(54) SINU BREATH

(76) Inventor: Teodoro A Unarce, Jr., San Jose, CA (US)

( * ) Notice: Subject to any disclaimer, the term of this patent is extended or adjusted under 35 U.S.C. 154(b) by 188 days.

(21) Appl. No.: 13/532,550

(22) Filed: Jun. 25, 2012

Related U.S. Application Data

(60) Provisional application No. 61/501,449, filed on Jun. 27, 2011.

(51) Int. Cl.
*A61N 1/20* (2006.01)
*A61N 1/37* (2006.01)

(52) U.S. Cl.
CPC .................................. *A61N 1/37* (2013.01)

(58) Field of Classification Search
USPC .......................................... 607/145, 149, 150
See application file for complete search history.

(56) References Cited

U.S. PATENT DOCUMENTS

| | | | | |
|---|---|---|---|---|
| 4,926,880 | A * | 5/1990 | Claude et al. | 607/148 |
| 5,243,130 | A * | 9/1993 | Kitagawa | 174/50 |
| 7,450,990 | B2 * | 11/2008 | Czygan | 607/28 |
| 2013/0197341 | A1 * | 8/2013 | Grob et al. | 600/391 |

OTHER PUBLICATIONS

Microchip Technologies. "PIC16F685/687/689/690 Data Sheet." Mar. 1, 2005. http://ww1.microchip.com/downloads/en/devicedoc/41262a.pdf.*

Toshiba. "2SC1815 Data Sheet." Apr. 10, 1997. http://html.alldatasheet.com/html-pdf/30084/TOSHIBA/C1815/244/1/C1815.html.*

* cited by examiner

*Primary Examiner* — Christopher D Koharski
*Assistant Examiner* — Michael Carey

(57) ABSTRACT

A handheld apparatus (100) provides a treatment level current to an outer conductive surface of the human body and includes an electrically conductive polyvinyl case (105) that provides a handhold to a user and an electrical ground to an apparatus circuit contained therein, the electrically conductive polyvinyl case (105) being electrically connected to a metal probe tip (170) which is electrically connected to a microchip (210) which provides the treatment level current to the metal probe tip, the treatment level current traveling through the outer conductive surface of the human body with the electrically conductive polyvinyl case (105) completing the apparatus circuit.

8 Claims, 8 Drawing Sheets

US 9,002,479 B1

SINU BREATH

CROSS-REFERENCE TO RELATED APPLICATIONS

This application claims the benefit of priority of U.S. Provisional Application Ser. No. 61/501,449 titled "SINU-BREATH" filed Jun. 27, 2011, which is incorporated by reference.

BACKGROUND

1. Field of Invention

This invention relates to the field of devices for applying microcurrents to the human body, and among other uses, specifically for applying microcurrents to the face to relieve sinus congestion.

2. Related Art

Humans have intentionally applied electricity to the human body for many years. Moderate levels of electricity applies across the heart may restart a heart stopped by shock or injury. Low levels of static electrically strategically placed above the head may provide entertainment by raising hair. Microcurrents may be applied to the face to relieve sinus and nasal congestion, as disclosed by U.S. Pat. No. 4,926,880. Technical advancements can improve such devices to provide better function and easier use.

SUMMARY OF THE INVENTION

The apparatus comprises an electrically inductive case that can be held and used in one hand, a low-power source, power level indicator, power switch, a conductive tip, and circuitry for providing microcurrents to the human body.

The apparatus may comprise an Electrically Conductive Polyvinyl Clamshell Case (105) which is electrically connected to At Least One Battery (110) having a plurality of power levels and which is electrically connected to a Printed Circuit Board (115), on which there is a Power Button (120) which electrically isolates the At Least One Battery (110) from a Metal Probe Tip (170) which is electrically connected to a Power Adjust Button (130) which adjusts the power level from the At Least One Battery (110) to a Microchip (210) which illuminates a red Low-Battery Power Light (150) which illuminates when the At Least One Battery (110) has a low power level and one of five Treatment Power Level Lights (140) which show the power level from the At Least One Battery (110) to the Metal Probe Tip (170), which is electrically connected to a plurality of green Treatment Lights (160) which are electrically connected to the At Least One Battery (110) which illuminate when the Microchip (210) applies power from the At Least One Battery (110) to the Metal Probe Tip (170) which conducts a treatment level current with the Electrically Conductive Polyvinyl Clamshell Case (105) completing an electrical circuit.

In some embodiments, the treatment level current is applied for 15 seconds.

In some embodiments, a Sound Button (125) is electrically connected to a Speaker (145) that emits an audible beeping sound when the Metal Probe Tip (170) is conducting the treatment level current for 15 seconds with the Electrically Conductive Polyvinyl Clamshell Case (105) completing an electrical circuit.

In some embodiments, a Sound Button (125) is electrically connected to a Speaker (145) that clicks when the metal probe tip (170) is conducting the treatment level current for 15 seconds with the Electrically Conductive Polyvinyl Clamshell Case (105) completing an electrical circuit.

In some embodiments, the Electrically Conductive Polyvinyl Clamshell Case (105) has an impedance of 70 ohms.

In some embodiments, the Electrically Conductive Polyvinyl Clamshell Case (105) is gray.

In some embodiments, the Electrically Conductive Polyvinyl Clamshell Case (105) is black.

DETAILED DESCRIPTION OF THE INVENTION

Figure 1:
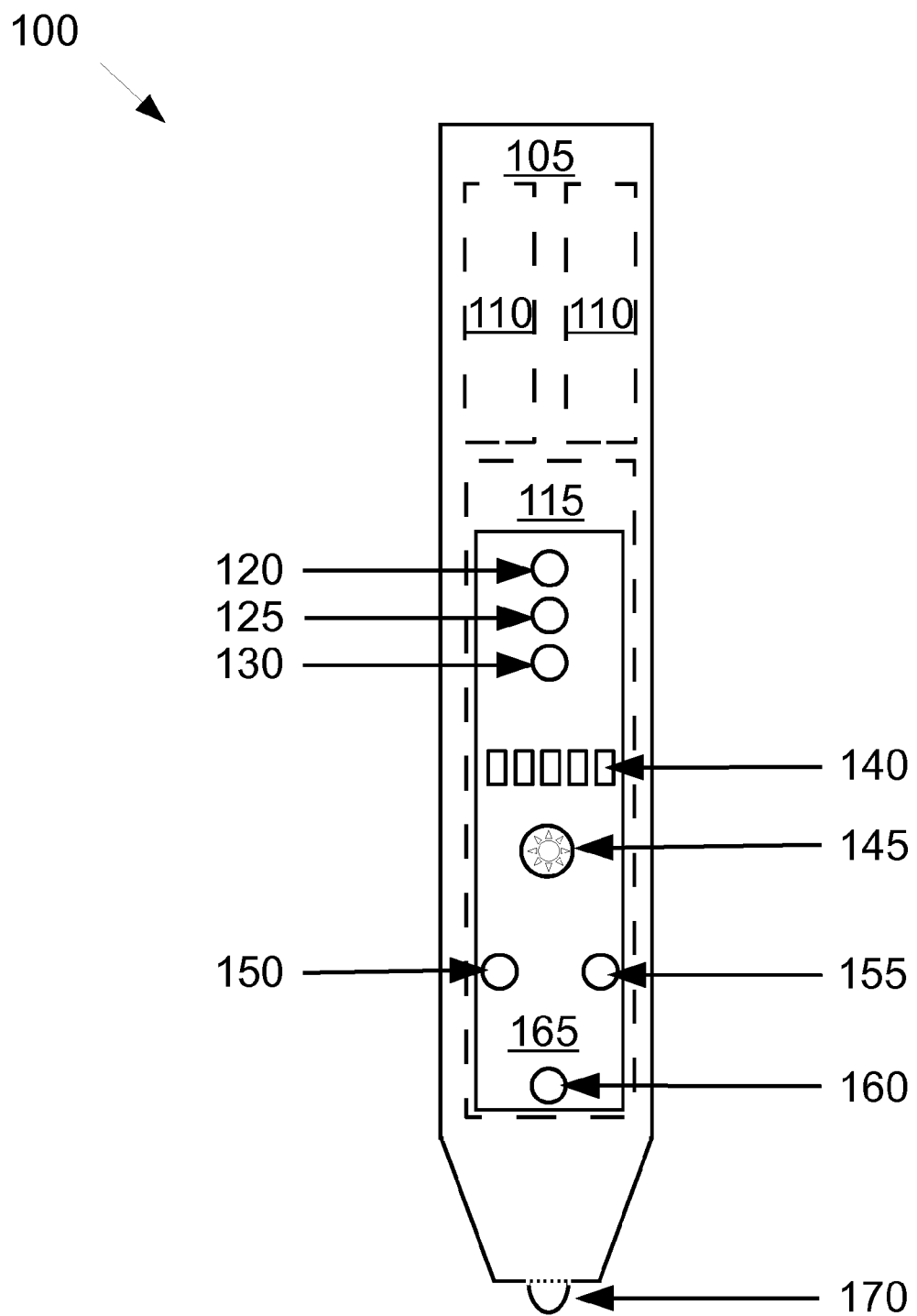
FIG. 1 shows an outer view of an embodiment for an apparatus for conducting a treatment level current to an outer conductive surface of the human body.

FIG. 1 shows an exemplary outside view of the Apparatus (100) for conducting a treatment level current to an outer conductive surface of the human body.

As shown in the FIG. 1 outer view, the apparatus (100) comprises an Electrically Conductive Polyvinyl Clamshell Case (105). The Electrically Conductive Polyvinyl Clamshell Case (105) serves as a container of the electrical components (FIGS. 2, 3A, 3B, 3C and 4) of the Apparatus (100), a handhold for using the Apparatus (100) and as an electrical ground for the device. The Electrically Conductive Polyvinyl Clamshell Case (105) may be made of PVC from Kwang Lin Scientific in Kaosaiung, Taiwan. The product name may be SINU-BREATH.

Shown in dashed lines, as these are inside the Electrically Conductive Polyvinyl Clamshell Case (105), is the At Least One Battery (110). The At Least One Battery (110) provides electrical energy to the Apparatus (100). The At Least One Battery (110) may be one or more batteries. The At Least One Battery (110) has a plurality of power levels, such as low, medium-low, medium, medium-high, high, i.e., full charge, or the plurality of power levels may be expressed numerically as a voltage or amperage, or other unit for measuring electrical charge.

The At Least One Battery (110) is electrically connected to the Electrically Conductive Polyvinyl Clamshell Case (105), and to a Printed Circuit Board (115), which is also electrically connected to the Electrically Conductive Polyvinyl Clamshell Case (105). The Printed Circuit Board (115) contains the circuit layout as shown in FIG. 3.

On the outside of the Electrically Conductive Polyvinyl Clamshell Case (105) is a Power Button (120). The Power Button (120) electrically isolates the At Least One Battery (110) from the rest of the electrical circuit of the Apparatus (100), which is shown in FIGS. 3A, 3B, 3C and 4.

Also on the outside of the Electrically Conductive Polyvinyl Clamshell Case (105) is a Sound Button (125) that may be set to "Tone" or alternately to "Click". At the "Tone" setting, a Speaker (145) emits an audible beeping sound when a treatment level current is being conducted to an outer conductive surface of the human body. At the "Click" setting, the Speaker (145) emits a clicking sound when a treatment level current is being conducted to an outer conductive surface of the human body.

Also on the outside of the Electrically Conductive Polyvinyl Clamshell Case (105) is a Power Adjust Button (130). The Power Adjust Button (130) adjusts the power to control the treatment level current being conducted to an outer conductive surface of the human body. In some embodiments, pressing the Power Adjust Button (130) toggles the treatment level current through five power setting for the power being conducted to an outer conductive surface of the human body.

Also on the outside of the Electrically Conductive Polyvinyl Clamshell Case (105) is a plurality of Treatment Power Level Lights (140). In a preferred embodiment, there are five green LEDs comprising the plurality of the Treatment Power Level Lights (140). One or more of the five Treatment Power Level Lights (140) illuminate to show the discharge power of the Apparatus (100) when a treatment level current is being conducted to an outer conductive surface of the human body. The Treatment Power Level Lights (140) may illuminate to show low, medium-low, medium, medium-high, or high power. In some embodiments, the Treatment Power Level Lights (140) may illuminate to numerically represent the power level as a voltage or amperage.

Also on the outside of the Electrically Conductive Polyvinyl Clamshell Case (105) is a Low-Battery Power Light (150) that illuminates when the At Least One Battery (110) has a low power level.

Also on the outside of the Electrically Conductive Polyvinyl Clamshell Case (105) is a Power Indicator Light (155), which illuminates when the Power Button (120) is in the ON position.

Also on the outside of the Electrically Conductive Polyvinyl Clamshell Case (105) is a plurality of green Treatment Lights (160). In a preferred embodiment, there are two green Treatment Lights (160), one on an Instrument Panel (165) on an upper surface of the Electrically Conductive Polyvinyl Clamshell Case (105) and another on a lower surface (220) of the Electrically Conductive Polyvinyl Clamshell Case (105) facing 180 degrees from the Instrument Panel (165). In the preferred embodiment, the plurality of green Treatment Lights are LEDs (8 and 9 on FIG. 3) and are electrically connected to the At Least One Battery (110) and illuminate when a treatment level current is being conducted to an outer conductive surface of the human body.

At the tip of the Electrically Conductive Polyvinyl Clamshell case (105) is a Metal Probe Tip (170). The Metal Probe Tip (170) conducts treatment level current from the apparatus (100) to an outer conductive surface of the human body. In some embodiments, the Metal Probe Tip (170) may be copper, aluminum, gold, silver, bronze, or any conductive metal. In some embodiments, the Metal Probe Tip (170) may be non-metallic in substance, e.g., glass or plastic, but coated with a conducting metallic material. In some embodiments, the Metal Probe Tip (170) may comprise a conductive but non-metal material.

Figure 2:
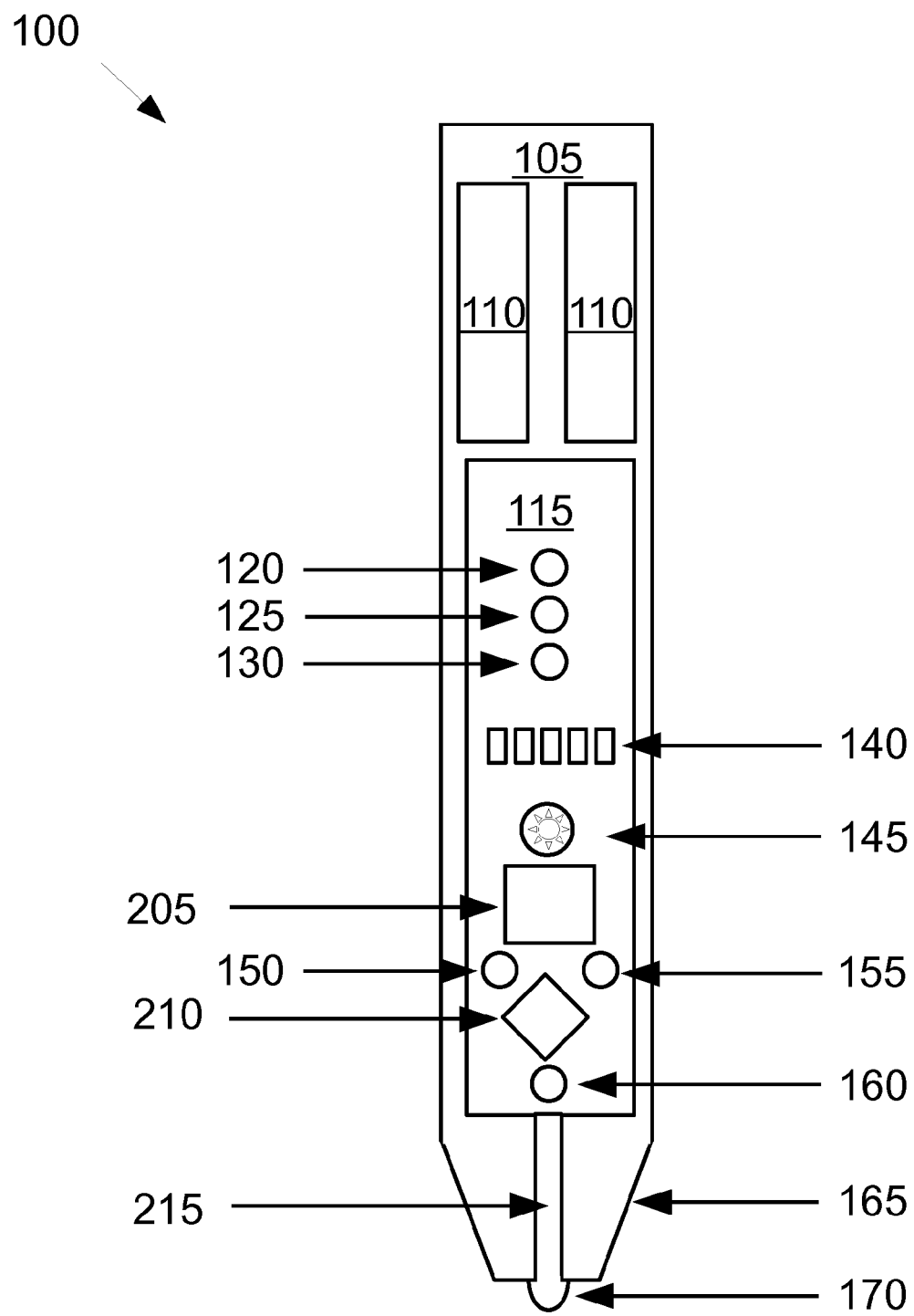
FIG. 2 shows an inner view of an embodiment for an apparatus for conducting a treatment level current to an outer conductive surface of the human body.

FIG. 2 shows an exemplary inside view of the Apparatus (100) for conducting a treatment level current to an outer conductive surface of the human body.

Shown now in solid lines, as they are visible on the inside of the Apparatus (100), are the At Least One Battery (110) and the Printed Circuit Board (115). Also appearing in FIG. 2 are the components of FIG. 1, as they are electrically connected to the Printed Circuit Board (115). For this reason, they also appear in FIG. 2. As these components were discussed with FIG. 1, only further detail on them will appear in the FIG. 2 discussion.

Also shown in FIG. 2 are the major electrical components of the Apparatus (100). These are a Power Converter (205), a Microchip (210), and a Metal Probe (215).

The Power Converter (205) receives power from the At Least One Battery (110) when the Power Button (120) is ON, and the Power Adjust Button (130) is set to discharge a minimal setting or more of treatment level current to be conducted to an outer conductive surface of the human body. When the Power Button (120) is ON, the Microchip (210) sends power to the Power Converter (205), which converts battery power from the At Least One Battery (110) to a treatment level current to be conducted to an outer conductive surface of the human body. To achieve this, the Power Converter (205) comprises in some embodiments, a plurality of coils. The plurality of coils receive one level of voltage and current at one set of coils, and discharges a different level of voltage and current to the Metal Probe (215) and next to the Metal Probe Tip (170) so that a treatment level current is conducted to an outer conductive surface of the human body.

The Microchip (210) (shown in greater detail in FIGS. 3 and 4) receives power from the At Least One Battery (110) and operational signals from the Power Button (120), the Sound Button (125), and the Power Adjust Button (130). With this power and signals, the Microchip (210) controls power and signals to the Treatment Power Level Lights (140), the Speaker (145), the Low-Battery Power Light (150), the Power Indicator Light (155), the plurality of green Treatment Lights (160) and the Metal Probe Tip (170) to discharge a treatment level current to be conducted to an outer conductive surface of the human body.

When the Power Button (120) is engaged, the Microchip (210) performs a self-test. If the battery power level is too low, the Microchip (210) causes the Low-Battery Power Light (150) to illuminate. If the battery power is acceptable and the rest of the circuitry passes the self-test, the Microchip (210) causes the Power Indicator Light (155) to illuminate.

Based on the operational signal from the Power Adjust Button (130), the Microchip (210) causes one or more of the Treatment Power Level Lights (140) to illuminate corresponding to the power level set by the Power Adjust Button (130).

From the Power Converter (205), the treatment level current is conducted to a Metal Probe (215), then to the Metal Probe Tip (170) and then an outer conductive surface of the human body. In some embodiments, the Metal Probe (215) may be same composition as the Metal Probe Tip (170). In some embodiments, the Metal Probe (215) may be a different composition from the Metal Probe Tip (170). In some embodiments, the Metal Probe (215) may be copper, aluminum, gold, silver, bronze, or any conductive metal. In some embodiments, the Metal Probe (215) may be non-metallic in substance, e.g., glass or plastic, but coated with a conducting metallic material. In some embodiments, the Metal Probe (215) may comprise a conductive but non-metal material.

Figure 3A:
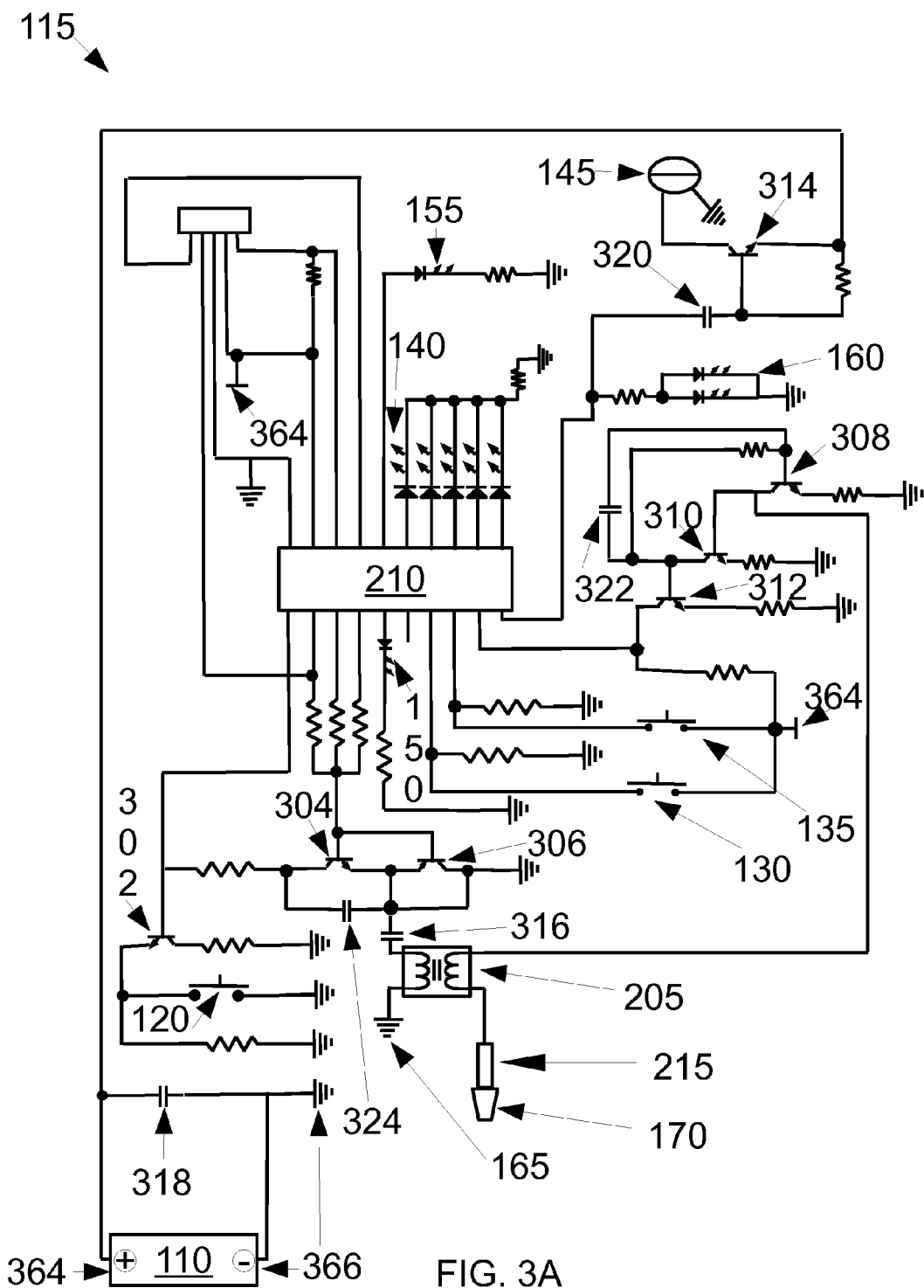
FIG. 3A, FIG. 3B, and FIG. 3C show a schematic of an embodiment for an apparatus for conducting a treatment level current to an outer conductive surface of the human body.
Figure 3B:
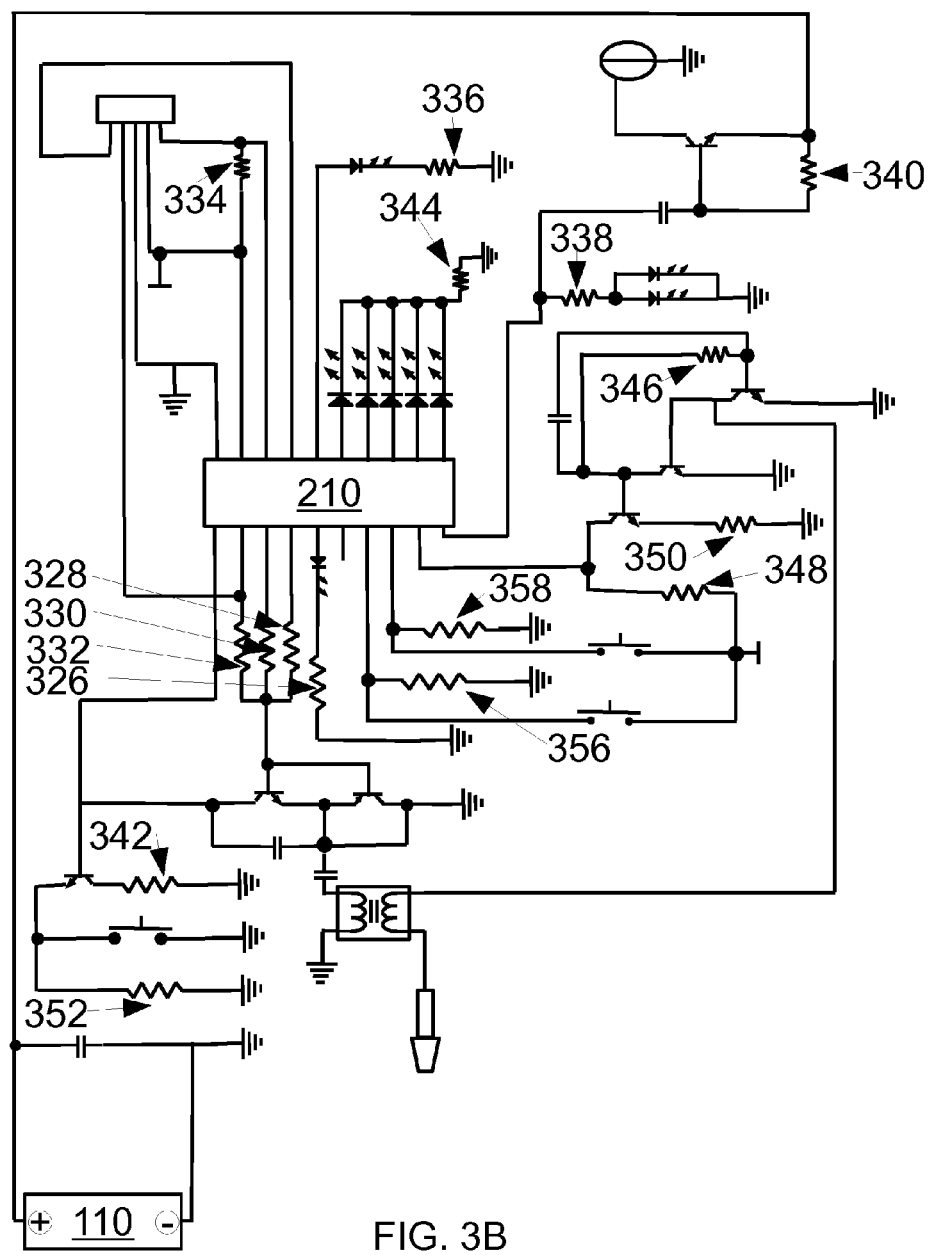
Figure 3C:
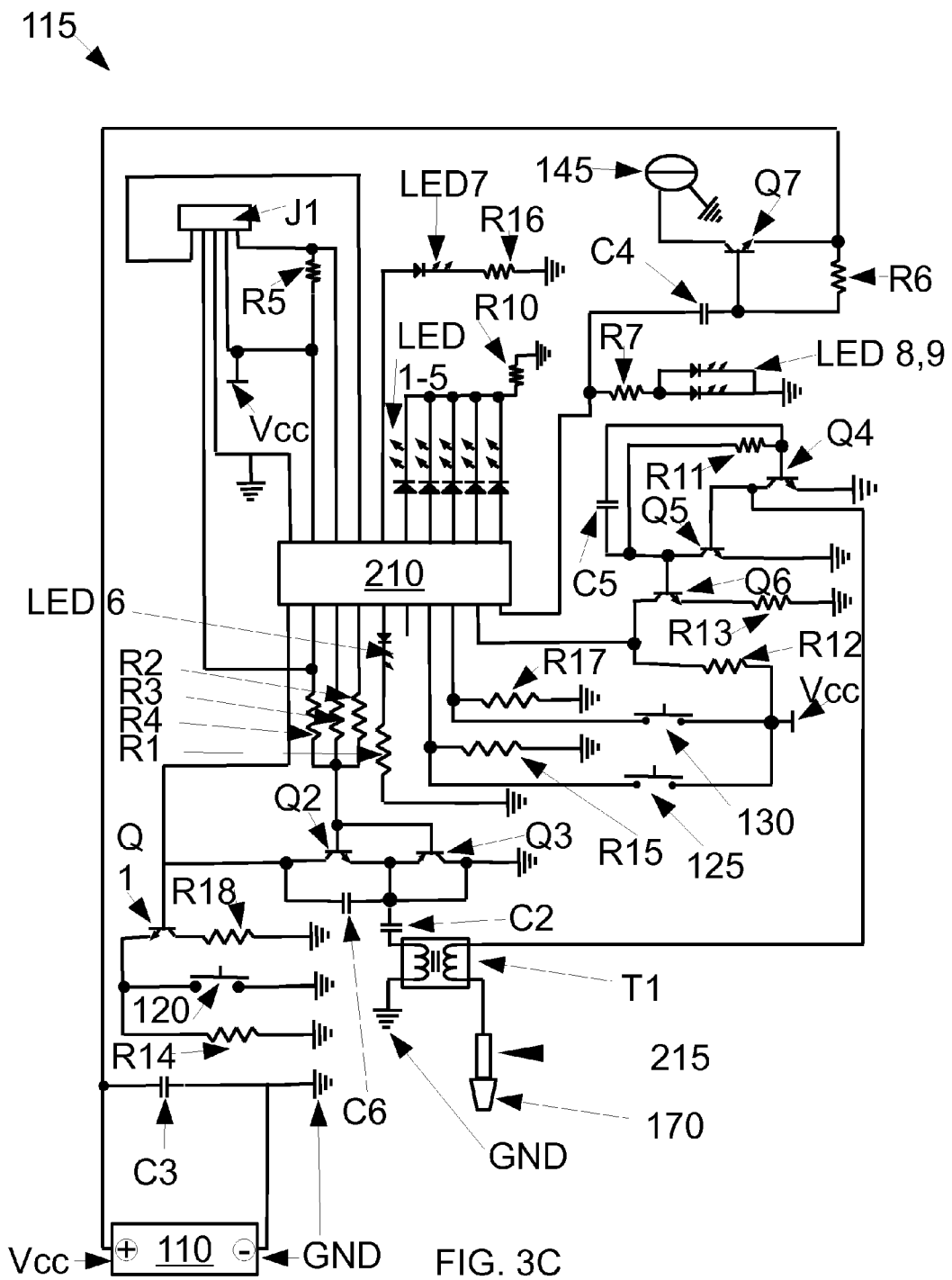
Figure 4:
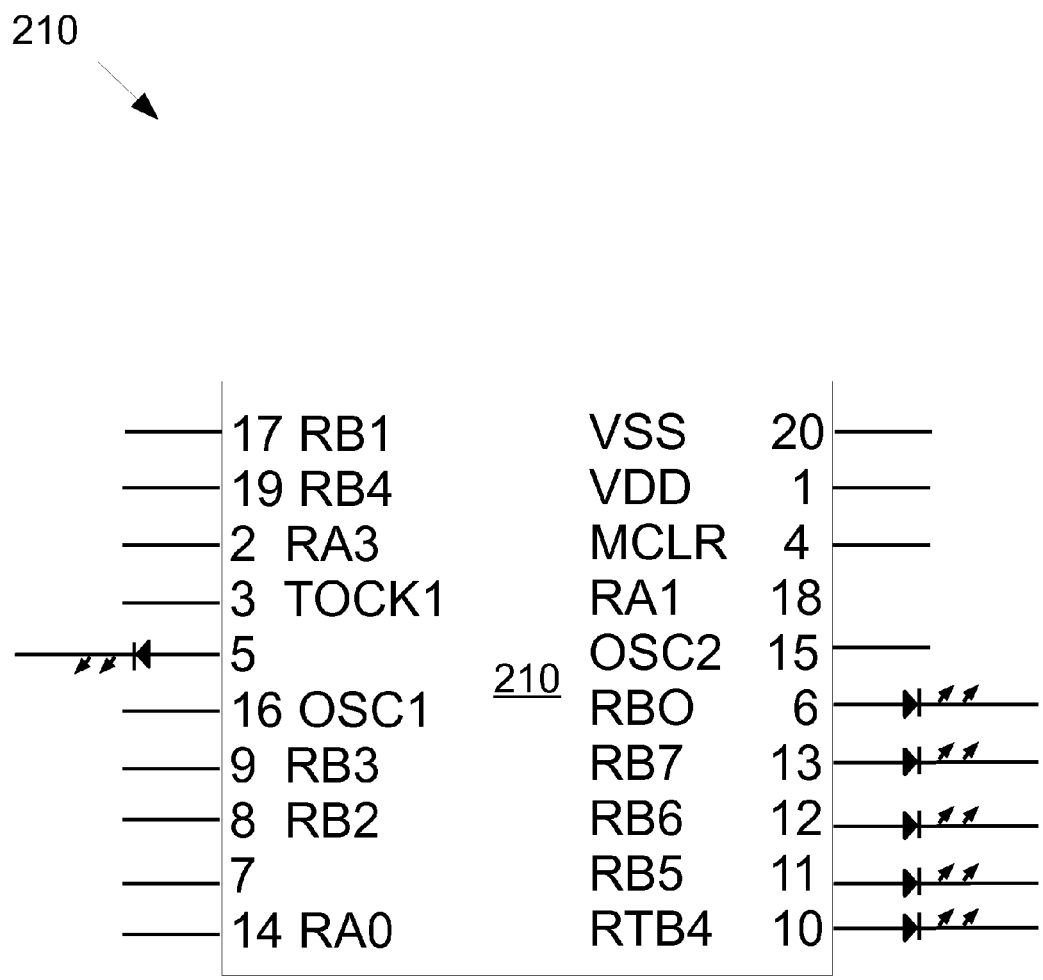
FIG. 4 shows a detail schematic of connections for a microchip used in an embodiment of an apparatus for conducting a treatment level current to an outer conductive surface of the human body.

The figures FIGS. 3A, 3B and 3C show an exemplary schematic of a plurality of electronic components present on the Printed Circuit Board (115) of the apparatus for conducting a treatment level current to an outer conductive surface of the human body.

FIG. 3A shows the components with numbered references for the electronic components except resistors. FIG. 3B shows the components with numbered references for the resistors. FIG. 3B shows the components using typical electronic component references.

Shown in the figures FIGS. 3A, 3B and 3C are the following electronic components.

Six C1815 NPN transistors (302, 304, 306, 308, 310, and 312, as Q1-Q6),
One A1015 NPN transistor (314, Q7),
One capacitor of 106 picofarads (316, C2),
One 6.3 volt capacitor of 100 microfarads (318, C3),
One capacitor of 106 picofarads (320, C4),
Two capacitors of 104 picofarads (322, 324 as C5-C6),
One resistor of 470 ohms (326, R1),
One resistor of 470 ohms (328, R2),
One resistor of 1500 ohms (330, R3),
One resistor of 3000 ohms (332, R4),
One resistor of 1500 ohms (334, R5),
One resistor of 1000 ohms (340, R6),
One resistor of 1000 ohms (338, R7),
One resistor of 150 ohms (344, R10),
One resistor of 1 million ohms (346, R11),
One resistor of 100K ohms (348, R12),
One resistor of 1000 ohms (350, R13),
One resistor of 1 million ohms (352, R14),
One resistor of 10K ohms (356, R15),
One resistor of 470 ohms (336, R16),
One resistor of 10K ohms (358, R17),
One resistor of 10K ohms (360, R18),
At least one positive power supply pin (364, VCC),
At least one ground pin (366, GND).
One junction plug (368, J1) which may be used for testing the apparatus or receiving inputs from the Power Button (120), Sound Button (125), and Power Adjust Button (130).

Also shown on the figures FIGS. 3A, 3B and 3C are certain electronic components as shown on FIG. 2. These are: five green LEDs (Treatment Power Level Lights (140, LED1-5) for showing the power level of the treatment current, one red LED (Low-Battery Power Light (150, LED6) for showing low battery power, one green Power Indicator Light (155, LED7) for showing the Apparatus (100) as ON, two green Treatment Lights (160, LED8&9) for showing a treatment level current is being discharged, and three push buttons (Power Button (120), Sound Button (125), and Power Adjust Button (130)).

These components are commercially available and may be used with standard specifications and tolerances.

The figures FIGS. 3A, 3B and 3C and FIG. 4 show the exemplary apparatus comprising at least one battery and a circuit ground and a microchip commercially designated as PIC16F690 having twenty electronic pins linearly designated as one through twenty. In addition, the pins designated as one through twenty are functionally designated and electrically connected via Printed Circuit Board (115) to electrical components of the Apparatus 100. The pin out arrangement of microchip commercially designated as PIC16F690 is as follows.

A pin linearly designated as 1 is functionally designated Vdd and is electrically connected to a positive supply voltage designated as Vcc which is electrically connected in parallel to a 1500 ohm resistor, with the 1500 ohm resistor then electrically connected in parallel to a pin linearly designated as 4 and to a test lead.

A pin linearly designated as 2 is functionally designated as RA3 and is electrically connected to a 1500 ohm resistor and is electrically connected in parallel to a pin 19 and a pin 3.

A pin linearly designated as 3 is functionally designated as TOCK1 and is electrically connected to a 470 ohm resistor and electrically connected in parallel to the pin 2 and to a pin linearly designated as 19.

A pin linearly designated as 4 is functionally designed as MCLR and is electrically connected in parallel to a test lead and to a 1500 ohm resistor which is electrically connected in parallel to the pin 1.

A pin linearly designated as 5 is electrically connected to a red Light Emitting Diode and a resistor having 470 ohms resistance, and the pin 5 electrically activates the red Light Emitting Diode when the at least one battery has a low power level.

A pin linearly designated as 6 is functionally designated as RB0 and is electrically connected to a green Light Emitting Diode which illuminates when the treatment level current is set to high, and which is electrically connected in parallel to a pin linearly designated as 13, a pin linearly designated as 12, a pin linearly designated as 11 and a pin linearly designated as 10, which are to serially connected to resistor having a resistance of 150 ohms and which is electrically connected to the circuit ground.

A pin linearly designated as 7 is electrically connected to a resistor having 100K ohms of resistance which is serially connected to a positive power supply of the at least one battery and the resistor having 100K ohms of resistance is electrically connected in parallel to a circuit of three transistors commercially designated as C1815 for outputting a treatment level current to an outer conductive surface of the human body.

A pin linearly designated as 8 is functionally designated as RB2 and is electrically connected to a resistor having 10K ohms of resistance which is electrically connected in parallel to a switch which is electrically connected to a positive supply voltage which is electrically connected in parallel to the pin 7 and is electrically connected in parallel to another switch which is similarly electrically connected in parallel to a resistor having 10K of ohms resistance and then to pin 9.

A pin linearly designated as 9 is functionally designated as RB3 and is electrically connected to a resistor having 10K ohms of resistance which is electrically connected in parallel to a switch for setting the treatment level current which is electrically connected to a positive supply voltage which is electrically connected in parallel to the pin 7 and is electrically connected in parallel to another switch for controlling an output sound which is similarly electrically connected in parallel to a resistor having 10K of ohms resistance and then to pin 8.

A pin linearly designated as 10 is functionally designated as RB4 and is electrically connected to a green Light Emitting Diode which illuminates when the treatment level current is set to low, and which is electrically connected in parallel to the pin linearly designated as 6, a pin linearly designated as 13, a pin linearly designated as 12 and a pin linearly designated as 11, which are serially connected to resistor having a resistance of 150 ohms and which is electrically connected to the circuit ground.

A pin linearly designated as 11 is functionally designated as RB5 and is electrically connected to a green Light Emitting Diode which illuminates when the treatment level current is set to medium-low, and which is electrically connected in parallel to the pin linearly designated as 6, a pin linearly designated as 13, a pin linearly designated as 12 and a pin linearly designated as 10, which are serially connected to resistor having a resistance of 150 ohms and which is electrically connected to the circuit ground.

A pin linearly designated as 12 is functionally designated as RB6 and is electrically connected to a green Light Emitting Diode which illuminates when the treatment level current is set to medium, and which is electrically connected in parallel to the pin linearly designated as 6, a pin linearly designated as 13, a pin linearly designated as 11 and a pin linearly designated as 10, which are serially connected to resistor having a resistance of 150 ohms and which is electrically connected to the circuit ground.

A pin linearly designated as 13 is functionally designated as RB7 and is electrically connected to a green Light Emitting Diode which illuminates when the treatment level current is set to medium-high, and which is electrically connected in parallel to the pin linearly designated as 6, a pin linearly designated as 12, a pin linearly designated as 11 and a pin linearly designated as 10, which are serially connected to resistor having a resistance of 150 ohms and which is electrically connected to the circuit ground.

A pin linearly designated as 14 is functionally designated as RA0 and is electrically connected in parallel to a first pin 14 circuit and to a second pin 14 circuit with the first pin 14 circuit comprising a resistor having 1K ohms of resistance which is connected to a pair of Light Emitting Diodes connected in parallel which illuminate when the apparatus applies a treatment level current to an outer conductive surface of the human body, and the second pin 14 circuit comprising a capacitor having $10^5$ picofards of capacitance electrically connected a resistor having 1K ohms of resistance connected in parallel to a transistor designated as A1015 which powers a buzzer when the apparatus applies a treatment level current to an outer conductive surface of the human body.

A pin linearly designated as 15 is functionally designated as OSC2 and is electrically connected to a green Light Emitting Diode which is electrically connected in series to a resistor having 470 ohms of resistance for illuminating the green Light Emitting Diode when the at least one battery is providing power to the apparatus (100).

A pin linearly designated as 16 is functionally designated as OSBC1 and is connected to the circuit ground.

A pin linearly designated as 17 is functionally designated as RB1 and is electrically connected in parallel to a first pin 17 circuit and a second pin 17 circuit, the first pin 17 circuit comprising a C1815 transistor electrically connected to an ON/OFF switch and the second pin 17 circuit comprising a resistor having 10K ohms of resistance connected to a plurality of circuits for powering a transformer to apply a treatment level current to an outer conductive surface of the human body.

A pin linearly designated as 18 is functionally designated as RA1 and is electrically connected to a test lead.

A pin linearly designated as 19 is functionally designated as RA4 and is electrically connected to a 3000 ohm resistor and electrically connected in parallel to the pins 2 and a pin 3, and A pin linearly designated as 20 is functionally designated as Vss and which is electrically connected to the circuit ground of the apparatus and to a test lead.

Figure 5:
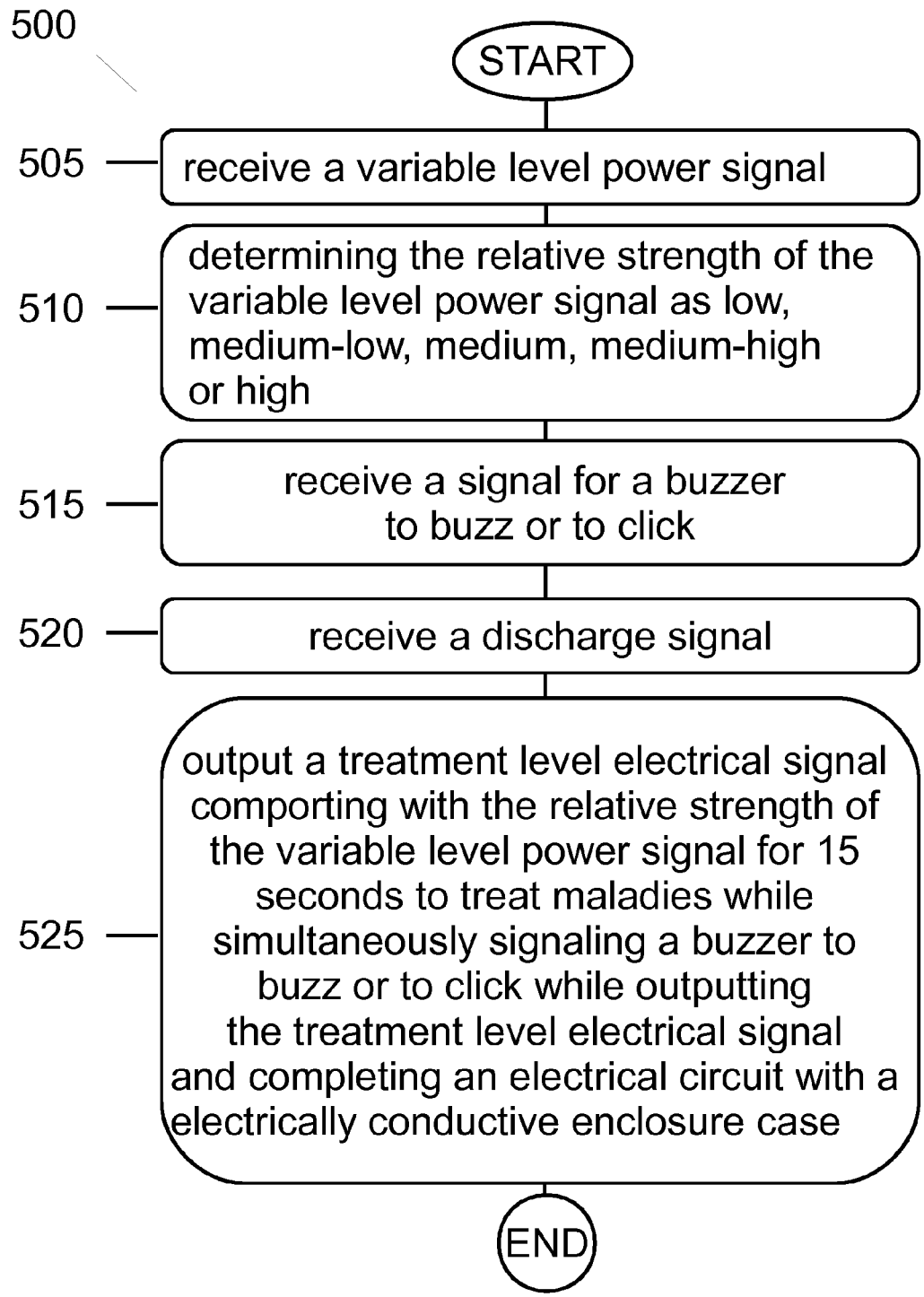
FIG. 5 shows a process for the treatment of maladies with electricity using the present invention.

FIG. 5 shows an exemplary process for the treatment of maladies with electricity. The process comprises the following steps.

At Step 505: receiving a variable level power signal.

At Step 510: determining the relative strength of the variable level power signal as low, medium-low, medium, medium-high or high.

At Step 515: receiving a signal for a buzzer to buzz or to click.

At Step 520: receiving a discharge signal.

At Step 525: outputting a treatment level electrical signal comporting with the relative strength of the variable level power signal for 15 seconds while simultaneously signaling a buzzer to buzz or click while outputting the treatment level electrical signal and completing an electrical circuit with an electrically conductive enclosure case.

Figure 6:
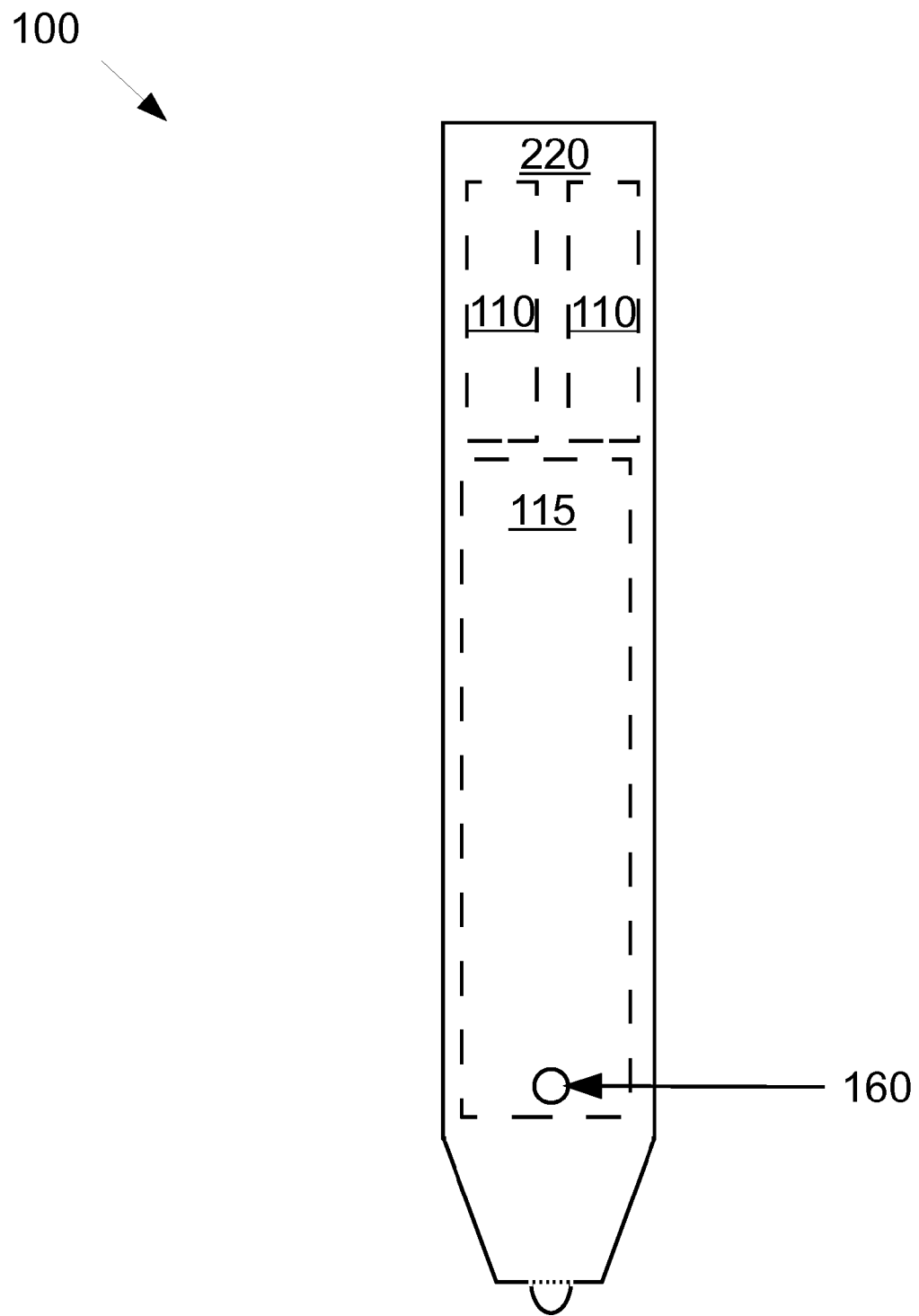
FIG. 6 shows an outer view of a back panel for an apparatus for conducting a treatment level current to an outer conductive surface of the human body.

FIG. 6 shows the lower surface (220) of the Electrically Conductive Polyvinyl Clamshell Case (105) facing 180 degrees from the Instrument Panel (165). On this lower surface (220) is a green Treatment Light (160). As with the green Treatment Light (160) on the Instrument Panel (165), the plurality of green Treatment Lights are LEDs (8 and 9 on FIG. 3) are electrically connected to the At Least One Battery (110) and illuminate when a treatment level current is being conducted to an outer conductive surface of the human body.

The embodiments discussed here are illustrative of the present invention. Elements in the figures are illustrated for simplicity and clarity and are not drawn to scale. Some elements may be exaggerated to improve the understanding of various embodiments. The descriptions and illustrations, as well as the various modifications or adaptations of the methods and/or specific structures described are within the spirit and scope of the present invention. Hence, these descriptions and drawings should not be considered in a limiting sense, as it is understood that the present invention is in no way limited to only the embodiments illustrated.

What is claimed is:

1. A handheld apparatus (100) providing a treatment level current to an outer conductive surface of the human body comprising:
   a case (105), the case (105) consisting of an electrically conductive polyvinyl material, the case (105) providing a handhold to a user and an electrical ground to an apparatus circuit contained therein, the case (105) being electrically connected to a metal probe tip (170) which is electrically connected to a microchip (210) which provides the treatment level current to the metal probe tip, the treatment level current traveling through the outer conductive surface of the human body with the case (105) completing the apparatus circuit.

2. The apparatus of claim 1 wherein the treatment level current is approximately 75 volts.

3. The apparatus of claim 1 wherein the treatment level current is applied for 15 seconds.

4. The apparatus of claim 1 further comprising a sound button (125) which is electrically connected to a speaker (145) which emits an audible beeping sound when the metal prove tip (170) is conducting the treatment level current for 15 seconds.

5. The apparatus of claim 1 further comprising a sound button (125) which is electrically connected to a speaker (145) which clicks when the metal prove tip (170) is conducting the treatment level current for 15 seconds.

6. The apparatus of claim 1 wherein the case (105) has an impedance of 70 ohms.

7. The apparatus of claim 1 further comprising a power adjust button (130) which adjusts the treatment level current and a plurality of treatment level lights (140) that illuminate to numerically represent the treatment level.

8. A process for providing a treatment level current to an outer conductive surface of a user's body comprising the steps of:
   receiving a variable level power signal;
   determining the relative strength of the variable level power signal as low, medium-low, medium, medium-high or high; and outputting a treatment level current comporting with the relative strength of the variable level power signal through a metal probe to the outer conductive surface of the user's body and completing an electrical circuit with a case comprised of an electrically conductive polyvinyl material held in the user's hand.

\* \* \* \* \*